US00PP23868P3

(12) United States Plant Patent
Bradford

(10) Patent No.: US PP23,868 P3
(45) Date of Patent: Sep. 3, 2013

(54) PEACH TREE NAMED 'GLACIER QUEEN'

(50) Latin Name: *Prunus persica*
Varietal Denomination: Glacier Queen

(76) Inventor: Lowell Glen Bradford, Le Grand, CA (US)

( * ) Notice: Subject to any disclaimer, the term of this patent is extended or adjusted under 35 U.S.C. 154(b) by 119 days.

(21) Appl. No.: 13/374,011

(22) Filed: Dec. 8, 2011

(65) Prior Publication Data

US 2013/0152256 P1 Jun. 13, 2013

(51) Int. Cl.
*A01H 5/00* (2006.01)

(52) U.S. Cl.
USPC ..... Plt./196

(58) Field of Classification Search
USPC ..... Plt./196
See application file for complete search history.

(56) References Cited

U.S. PATENT DOCUMENTS

PP12,570 P2 4/2002 Bradford

*Primary Examiner* — June Hwu

(57) ABSTRACT

The present invention relates to a new and distinct variety of peach tree, *Prunus persica*, broadly characterized by a large size, vigorous, hardy, self-fertile, productive and regular bearing tree. The variety blooms during the early to mid season and requires about 450 chilling hours. The fruit matures under the ecological conditions described in late August, with first picking on Aug. 24, 2011. The fruit is uniform, very large in size, sub-acidic in flavor, globose in shape, freestone in type, firm and melting in texture, white in flesh color, mostly red in skin color, and good in flavor.

1 Drawing Sheet

Botanical classification: *Prunus persica.*
Variety denomination: 'GLACIER QUEEN'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of peach tree, which has been denominated varietally as 'Glacier Queen'.

The present variety was hybridized by me in 2000 as a first generation cross using 'Snow Princess' (U.S. Plant Pat. No. 12,570) peach as the selected seed parent and an unnamed yellow flesh freestone peach designated by code number '3P1236' (unpatented) as the selected pollen parent. The fruit of this cross was gathered that summer, and the seeds were removed, cracked, stratified, germinated, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 2004 I selected the present variety as a single tree from the group of seedlings described above. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its pollen parent, '3P1236' (unpatented) peach, by producing peaches that are large in size, firm in texture, globose in shape, freestone in type, and mostly red in skin color, but is quite distinguished therefrom by producing peaches that are white instead of yellow in flesh color and that are sub-acidic instead of acidic in flavor.

The present variety is most similar to its seed parent 'Snow Princess' peach (U.S. Plant Pat. No. 12,570) by producing fruit that is white in flesh color, mostly red in skin color, globose in shape, freestone in type, and sub-acidic in taste, but is distinguished therefrom by having globose instead of reniform leaf glands and by producing fruit that is somewhat larger in size and that matures about twenty days later. It is to be noted that the claimed ripening time for 'Snow Princess' peach in U.S. Plant Pat. No. 12,570 was Jul. 20, 2000. It has been determined during subsequent years that the ripening time for 'Snow Princess' peach is usually between August 1st and August 5th, with the actually date of first pick recorded this year as Aug. 5, 2011.

The present variety is similar to 'Pearl Princess V' peach (U.S. Plant Pat. No. 19,919) by producing fruit that is nearly white in flesh color, mostly red to pink in skin color, freestone in type, firm in texture, globose in shape, and has a bitter tasting kernel. However, the present variety differs from the 'Pearl Princess V' by having globose instead of reniform leaf glands, by requiring 450 chilling hours instead of 500, by producing fruit that is somewhat larger in size, and by maturing about 56 days later.

The present variety is similar to 'Snow Duchess' peach (U.S. Plant Pat. No. 17,281) by producing fruit that is nearly white in flesh color, mostly red to pink in skin color, freestone in type, firm in texture, globose in shape, and has a bitter tasting kernel. However, the present variety differs from 'Snow Duchess' by having globose instead of reniform leaf glands and by producing fruit that is much larger in size and that matures about ten days later.

SUMMARY OF VARIETY

In summary, the present variety is characterized by a large size, vigorous, hardy, self-fertile, productive and regular bearing tree. The variety blooms during the early to mid season and requires about 450 chilling hours. The fruit matures under the ecological conditions described in late August, with first picking on Aug. 24, 2011. The fruit is uniform, very large in size, sub-acidic in flavor, globose in shape, freestone in type, firm and melting in texture, white in flesh color, mostly red in skin color, and good in flavor.

DRAWING

The accompanying photograph consists of four whole fruits positioned to display the characteristics of the skin color and form, one divided fruit to reveal the flesh and stone, two insets to reveal buds and blossoms, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of somewhat overripe on Sep. 4, 2011, on the original tree during its eleventh growing season. The blossom and flower descriptions were made the previous blooming season. All major color code designations are by reference to the Inter-Society Color Council, National Bureau of Standards. Common color names are also used occasionally.

PARENTAGE

Seed parent: 'Snow Princess' (U.S. Plant Pat. No. 12,570) peach.

Pollen parent: '3P1236' (unpatented) peach.

TREE

Size: Large, reaching and maintaining a height of 10' [3.05 m.] and a spread of 10' [3.05 m.] after eleven growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 450 hours.

Trunk:

- *Size.*—Slender, reaching a maximum diameter of 6" [152.4 mm.] after the eleventh growing season.
- *Texture.*—Medium shaggy.
- *Bark color.*—A Dark grayish brown [62. d.gy.Br] and Dark brown [59. d.Br] variegation with Moderate orange yellow [71. m.OY] crevices present.
- *Lenticels.*—Approximate Number Per Square Inch: 9. Color: Light yellowish brown [76. l.yBr]. Average Size: ¼" [6.4 mm.] to 7/16" [11.1 mm.]. Shape: Eye-shaped, elongated.

Branches:

- *Size.*—Diameter of Main scaffold is 4¼" [108 mm.] measured 12" above the crotch, diameter of limb is 2¼" [63.8 mm.] measured 12" above the first fork.
- *Texture.*—Smooth on first and second year wood, increasing roughness with age.
- *Color.*—1st Year Wood Topside: Grayish red [19. gy.R]. 1st Year Wood Underside: Brilliant yellow green [116. brill.YG]. Older Wood: A Dark grayish yellowish brown [81. d.gy.yBr] and Dark yellowish brown [78. d.yBr] variegation.
- *Lenticels.*—Number Per Square Inch: About 60 on second year wood. Color: Light yellowish brown [76. l.yBr]. Size: 1/64" [0.4 mm.] to 1/16" [1.6 mm.] on second year wood. Shape: Eye-shaped, elongated.

Leaves:

- *Size.*—Large. Average Length: 6⅜" [161.9 mm.]. Average Width: 1 11/16" [42.9 mm.].
- *Arrangement.*—Alternate.
- *Thickness.*—Medium.
- *Form.*—Elliptical.
- *Apex.*—Acuminate.
- *Base.*—Acute, with an average base angle of 75 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Vein color.*—Pale yellow green [121. p.YG].
- *Petiole.*—Average Length: ½" [12.7 mm.]. Average Thickness: 1/16" [1.6 mm.]. Color: Very yellow green [115. v.YG].
- *Stipules.*—Number: Usually 2 per leaf, up to 6 per growing tip. Average Length: ⅜" [9.5 mm.]. Color: Light yellow green [119. l.YG] becoming Grayish brown [61. gy.Br] with maturity.
- *Glands.*—Number: 2 to 4 per leaf. Position: Alternately positioned on petiole and base of blade. Size: Small. Form: Globose. Color: Light yellow green [119. l.YG] becoming Grayish reddish brown [46. gy.rBr] with age.
- *Leaf buds.*—Pointed, medium in size.

Flower buds:

- *Hardiness.*—Hardy, with respect to central California winters.
- *Diameter.*—Typically ⅜" [9.5 mm.] 1 week before bloom.
- *Length.*—Typically 11/16" [17.5 mm.] 1 week before bloom.
- *Form.*—Not appressed.
- *Surface.*—Pubescent.
- *Tip color.*—Light purplish pink [249. l.pPk].

Flowers: Perfect, complete, perigynous, usually a single pistil, typically about thirty stamens, five sepal and petal locations alternately positioned.

- *Type.*—Showy, large.
- *Average flower diameter.*—2 1/16" [52.4 mm.].
- *Number of petals.*—Five, extra petal fragments are occasionally observed.
- *Petal shape.*—Circular to oval.

*Petal margin.*—Entire, very wavy, occasional notches.
*Average petal diameter.*—13/16" [20.6 mm.].
*Average petal length.*—7/8" [22.2 mm.].
*Petal apex.*—Rounded.
*Petal base.*—Rounded to somewhat truncate.
*Petal color.*—Pale pink [7. p.Pk] toward the apex, Light purplish pink [249. l.pPk] toward the base on both sides.
*Anther color.*—Light orange [52. l.O] over a Light yellow [86. l.Y] center at bloom onset.
*Stigma color.*—Pale yellow green [121. p.YG].
*Sepal color.*—Dark purplish red [259. d.pR] on the outer surface.
*Sepal length.*—1/4" [6.4 mm.].
*Sepal width.*—3/16" [4.8 mm.].
*Sepal apex.*—Rounded to elliptical to match the sepal length and width.
*Sepal margin.*—Fairly smooth.
*Average pistil length.*—11/16" [17.5 mm.].
*Average stamen length.*—9/16" [14.3 mm.].
*Fragrance.*—Moderate.
*Blooming period.*—Early to medium, three days after 'Snow Princess' (U.S. Plant Pat. No. 12,570) peach.
*Onset of bloom.*—One percent on Feb. 18, 2011.
*Date of full bloom.*—Feb. 26, 2011.
*Duration of bloom.*—One to two weeks, dependent on ambient temperature.
*Number per cluster.*—1 to 3 with single flowers most common.

FRUIT

Maturity when described: Somewhat overripe, Sep. 4, 2011.
Date of first picking: Aug. 24, 2011.
Date of last picking: Sep. 5, 2011.
Size: Uniform, very large.
*Average diameter axially.*—3 1/4" [82.6 mm.].
*Average diameter across suture plane.*—3 5/8" [92.1 mm.].
*Average diameter across cheek plane.*—3 5/8" [92.1 mm.].
*Typical weight.*—13.9 ounces [394 grams].
Form: Uniform, globose, symmetrical.
*Longitudinal section form.*—Circular to slightly oval.
*Axial view.*—Round.
Suture: A distinct line that extends from the base, along the side, to just beyond the pistil point.
*Near the base.*—A shallow groove.
*Along the side.*—A shallow trough.
*Near the apex.*—A shallow groove.
Ventral surface: Rounded, lipped toward the apex on both sides.
Lips: Slightly unequal.
Cavity: Flaring, elongated in the suture plane, suture showing on one sides, Pale yellowish pink [31. p.yPk] stem markings typical.
*Depth.*—9/16" [14.3 mm.].
*Breadth.*—1 3/8" [34.9 mm.].
Base: Truncate.
Apex: Rounded.
Pistil point: Oblique, very short in length, usually depressed within the suture.
Stem: Medium.
*Average length.*—3/8" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Non-astringent.
*Tendency to crack.*—Very slight.
*Color.*—Deep red [13. deep R] smoothly blending into Light yellowish pink [28. l.yPk].
*Down.*—Scant, short, does not roll up when rubbed.
Flesh:
*Color.*—White [263. White] acquiring Dark red [16. d.R] streaking toward stone with maturity.
*Surface of pit cavity.*—Covered with Moderate red [15. m.R] fibers.
*Amygdalin.*—Scarce.
*Juice.*—Moderate, rich.
*Texture.*—Firm, melting.
*Fibers.*—Abundant, fine, tender.
*Ripens.*—Earliest at apex.
*Flavor.*—Sweet, typically 16 to 18 brix.
*Aroma.*—Very slight.
*Eating quality.*—Good.

STONE

Type: Freestone.
Form: Oval.
Hilum: Oval.
Base: Straight.
Apex: Acuminate.
Sides: Equal.
Surface: Irregularly furrowed toward the apex and ventral edge, pitted toward the base.
Ridges: Jagged.
External color: Dark reddish brown [44. d.rBr].
Pit wall color when cracked: Deep brown [56. deep Br].
Cavity surface color: Strong brown [55. s.Br].
Average pit wall thickness: 1/4" [6.4 mm.].
Average width: 1 1/16" [27.0 m.].
Average length: 1 3/4" [44.5 mm.].
Average breadth: 11/16" [17.5 mm.].
Tendency to split: Very slight.
Kernel:
*Form.*—Oval.
*Skin color.*—Strong yellowish brown [74. s.yBr] when first removed.
*Pellicle color.*—Deep yellowish brown [75. deep yBr].
*Vein color.*—Deep yellowish brown [75. deep yBr].
*Taste.*—Bitter.
*Viable.*—Yes.
*Average width.*—9/16" [14.3 mm.].
*Average length.*—7/8" [22.2 mm.].
*Amygdalin.*—Moderate.

USE

Market: Fresh market and long distance shipping.
Keeping quality: Good, fruit quality observed to remain in good condition after 14 days in standard cold room at 36° Fahrenheit [2° Celsius].

Shipping quality: Good.
Resistance to insects: No unusual susceptibilities noted.
Resistance to diseases: No unusual susceptibilities noted.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to its seed parent 'Snow Princess' peach (U.S. Plant Pat. No. 12,570) by producing fruit that is white in flesh color, mostly red in skin color, globose in shape, freestone in type, and sub-acidic in taste, but is distinguished therefrom by having globose instead of reniform leaf glands and by producing fruit that is somewhat larger in size and that matures about twenty days later.

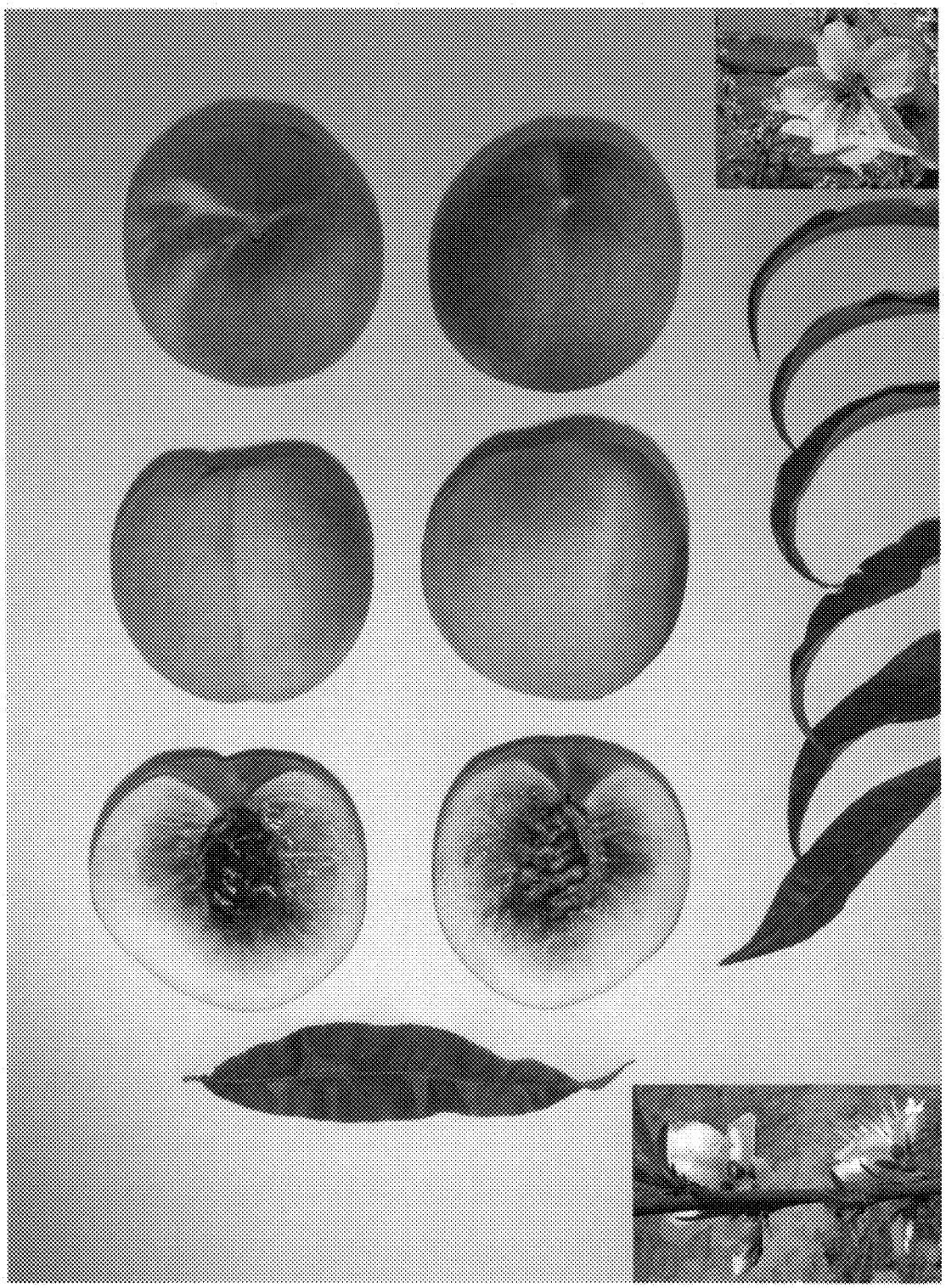

* * * * *